(12) United States Patent
Clowes et al.

(10) Patent No.: US 8,848,750 B2
(45) Date of Patent: *Sep. 30, 2014

(54) OPTICAL PULSE SOURCES

(75) Inventors: John Clowes, Southampton (GB); Anatoly Grudinin, Southampton (GB); Ian Godfrey, Southampton (GB)

(73) Assignee: Fianium Ltd., Southampton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/316,006

(22) Filed: Dec. 9, 2008

(65) Prior Publication Data

US 2009/0097512 A1 Apr. 16, 2009

(30) Foreign Application Priority Data

Jan. 19, 2008 (GB) .................................. 0800936.7

(51) Int. Cl.
| | |
|---|---|
| H01S 3/108 | (2006.01) |
| H01S 3/23 | (2006.01) |
| G02B 21/16 | (2006.01) |
| H01S 3/10 | (2006.01) |
| H01S 3/11 | (2006.01) |
| G02F 1/35 | (2006.01) |
| G01N 21/64 | (2006.01) |
| G02F 1/365 | (2006.01) |

(52) U.S. Cl.
CPC ........... *H01S 3/11* (2013.01); *G02F 2001/3528* (2013.01); *G01N 2201/0697* (2013.01); *G01N 21/6458* (2013.01); *H01S 3/2308* (2013.01); *G02B 21/16* (2013.01); *G02F 1/365* (2013.01); *H01S 3/10* (2013.01); *G02F 1/353* (2013.01); *G01N 2021/6419* (2013.01); *G01N 2021/6441* (2013.01)
USPC .................... 372/21; 372/6; 372/23

(58) Field of Classification Search
USPC ............................................ 372/21
See application file for complete search history.

(56) References Cited

U.S. PATENT DOCUMENTS 5,923,683 A * 7/1999 Morioka et al. ............... 372/6
6,097,870 A 8/2000 Ranka et al.

(Continued)

FOREIGN PATENT DOCUMENTS

| EP | 1720223 A1 | 7/2005 |
|---|---|---|
| GB | 2 434 483 A | 7/2007 |
| WO | WO 2005/119328 A1 | 12/2005 |

OTHER PUBLICATIONS

J. H. Frank et al., "A white light confocal microscope for spectrally resolved multidimensional imaging", Journal of Microscopy, vol. 227, Part 3, Sep. 2007, pp. 203-215.*

(Continued)

*Primary Examiner* — Xinning Niu
(74) *Attorney, Agent, or Firm* — Peter Rainville; Nicholas J. Tucillo

(57) ABSTRACT

An optical pulse source comprising a DPSS pump laser, a photonic crystal fiber (PCF), and acousto-optic modulator (AOM) gating device is disclosed. The pump pulses are coupled through lenses to the AOM gating device, which is synchronized to the pump laser and is operable to gate the pump pulses to a reduced repetition rate Rr=Rf/N, where Rf is the pump laser fundamental frequency. The pulses from the AOM are injected via optics into the PCF. Propagation through the PCF causes the pulses to broaden spectrally to produce optical supercontinuum pulses. An optical pulse source that further includes an acousto-optical tunable filter (AOTF) operable to convert the optical supercontinuum pulses into wavelength variable output pulses is also provided. A method of scaling the energy of the optical supercontinuum pulses is also disclosed.

48 Claims, 8 Drawing Sheets

(56) References Cited

U.S. PATENT DOCUMENTS

| | | | |
|---|---|---|---|
| 6,307,667 B1* | 10/2001 | Liang | 359/337 |
| 6,611,643 B2 | 8/2003 | Birk et al. | |
| 6,687,000 B1 | 2/2004 | White | |
| 6,690,463 B2* | 2/2004 | Kask | 356/317 |
| 7,088,491 B2* | 8/2006 | Takita et al. | 359/279 |
| 2003/0156605 A1* | 8/2003 | Richardson et al. | 372/25 |
| 2004/0065845 A1* | 4/2004 | Seyfried | 250/458.1 |
| 2004/0213302 A1* | 10/2004 | Fermann et al. | 372/6 |
| 2005/0041702 A1* | 2/2005 | Fermann et al. | 372/25 |
| 2005/0238070 A1* | 10/2005 | Imeshev et al. | 372/21 |
| 2005/0265407 A1 | 12/2005 | Braun et al. | |
| 2006/0120418 A1* | 6/2006 | Harter et al. | 372/30 |
| 2007/0025662 A1 | 2/2007 | Gugel | |

OTHER PUBLICATIONS

Xia et al., "Power scalable mid-infrared supercontinuum generation in ZBLAN fluoride fibers with up to 1.3 watts time-averaged power", Optics Express, vol. 15, No. 3, Feb. 2007, pp. 865-871.*

European Search Report from European Application No. 08 169 413.5, mailed Feb. 23, 2009.

Alfano, R. R., et al., "Observation of Self-Phase Modulation and Small-Scale Filaments in Crystals and Glasses", Physical Review Letters, vol. 24, No. 11, Mar. 1970, pp. 592-594.

Donnert, G., et al., "Macromolecular-scale Resolution in Biological Fluorescence Microscopy," PNAS, vol. 103, No. 31, Aug. 2006, pp. 11440-11445.

Frank, J. H., et al., "A white light confocal microscope for spectrally resolved multidimensional imaging", Journal of Microscopy, vol. 227, Part 3, Sep. 2007, pp. 203-215.

Kaminski, C. F., et al., "Supercontinuum radiation for applications in chemical sensing and microscopy", Applied Physics B, Laser and Optics, 92(3), 06, Aug. 2008, pp. 367-378.

Norris, T. B., "Femtosecond pulse amplification at 250 kHz with a Ti:sapphire regenerative amplifier and application to continuum generation", Optics Letters, vol. 17, No. 14, Jul. 1992, pp. 1009-1011.

Ranka, J. K., et al., "Efficient visible continuum generation in air-silica microstructure optical fibers with anomalous dispersion at 800 nm", CLEO '09, Conference in Baltimore, MD, May 1999.

Ranka, J. K., et al., "Visible continuum generation in air-silica microstructure optical fibers with anomalous dispersion at 800 nm", Optics Letters, vol. 25, No. 1, Jan. 2000, pp. 25-27.

Rusu, M., et al., "Slicing the supercontinuum radiation generated in photonic crystal fiber using an all-fiber chirped-pulse amplification system", Optics Express, vol. 13, No. 17, Aug. 2005.

Wadsworth, W. J., et al., "Supercontinuum and four-wave mixing with Q-switched pulses in endlessly single-mode photonic crystal fibers", Optics Express, vol. 12, No. 2, Jan. 2004.

Wildanger, D., et al., "STED microscopy with a supercontinuum laser source", Optics Express, vol. 16, No. 13, Jun. 2008.

Communication pursuant to Article 94(3) EPC, European Patent Office, May 2, 2011 Application No. 08169413.5-2205.

Elson, et al., "Fluorescence lifetime system for microscopy and multiwell plate imaging with a blue picosecond diode laser", Optics Letters, vol. 27 No. 16, Aug. 15, 2002.

Response of Jan. 17, 2012 to Hegner,Observations pursuant to Article 115 EPC filed in EP Application No. 08169413.5 (EP2081074) Nov. 1, 2011 (11 pages).

Amended claims accompanying Response of Jan. 17, 2012 to Hegner,Observations pursuant to Article 115 EPC filed in EP Application No. 08169413.5 (EP2081074) Nov. 1, 2011 (6 pages).

Hegner, Anette, Letter and Observations, Feb. 16, 2011.

Xia, Chenan et al., "Power scalable mid-infrared supercontinuum generation in ZBLAN fluoride fibers with up to 1.3 watts time-averaged power", Optics Express, vol. 13, No. 3, Feb. 5, 2007.

Borlinghaus, Rolf, "Closing the spectral gap—the transition from fixed-parameter fluorescence to tunable devices in confocal microscopy", SPIE, vol. 6090 (2006).

Price, J.H.V., "Soliton transmission and supercontinuum generation in holey fiber, using a diode pumped Ytterbium fiber source", Optics Express, vol. 10, No. 8, Apr. 22, 2002.

T.V. Andersen et al., "High repetition rate tunable femtosecond pulses and broadband amplification from fiber laser pumped parametric amplifier", Optics Express, vol. 14, No. 11, p. 4765-4773, May 2006.

Part I—Hegner,Observations pursuant to Article 115 EPC filed in EP Application No. 08169413.5 (EP2081074) Nov. 1, 2011 (11 of 26 total pages).

Response to Communication pursuant to Art. 94(3) EPC in EP Application No. 08169413.5 (EP2081074) Sep. 12, 2011 (13 pages).

Claims accompanying Response to Communication pursuant to Art. 94(3) EPC in EP Application No. 08169413.5 (EP2081074) Sep. 12, 2011 (6 pages).

Specification Amendments accompanying Response to Communication pursuant to Art. 94(3) EPC in EP Application No. 08169413.5 (EP2081074) Sep. 12, 2011 (5 pages).

Part II—Hegner,Observations pursuant to Article 115 EPC filed in EP Application No. 08169413.5 (EP2081074) Nov. 1, 2011 (15 of 26 total pages).

Observations and prior art with relevance to European patent application EP 08169413.5, Aug. 24, 2012 (14 pgs).

Stanford Research Systems, Data sheet, "Digital Delay/Pulse Generator DG535" (4 pgs).

Stanford Research Systems, Product Manual "Model DG535 Digital Delay/Pulse Generator", Sunnyvale, CA, Revision 2.9, Feb. 2006 (54 pgs).

Agilent Technologies, Web Print-out, "8131A High-Speed Pulse Generator, 500 MHz", 2000-2012 (1 pg).

Jonathan Hugh Vaughan Price, "The Development of High Power, Pulsed Fiber Laser Systems and their Applications," University of Southampton, Optoelectronics Research Centre, Doctor of Philosophy Thesis, Jul. 2003 (181 pgs).

Letter accompanying subsequently filed items, Application No. 08169413.5, Hegner & Partners A/S, Sep. 4, 2012 (1 pg).

EPO Form 2906—Annex to Summons to Oral Proceedings—in EP Application No. 08169413.5 (EP2081074) Aug. 24, 2012 (7 pages).

Dunsby, C., et al., "An electronically tunable ultrafast laser source applied to fluorescence imaging and fluorescence lifetime imaging microscopy", Journal of Physics D: Applied Physics, vol. 37, pp. 3296-3303, Nov. 19, 2004.

Communication Pursuant to Article 94(3) EPC in EP Application No. 08169413.5 (EP2081074) Feb. 16, 2012 (5 pages).

Response to Communication Pursuant to Article 94(3) EPC in EP Application No. 08169413.5 (EP2081074) Jun. 26, 2012 (11 pages).

Claims Accompanying Response to Communication Pursuant to Article 94(3) EPC in EP Application No. 08169413.5 (EP2081074) Jun. 26, 2012 (6 pages).

EPO Findings Regarding Oral Proceedings, Nov. 12, 2012 (2pgs).

EPO Communication Regarding Oral Proceedings, Nov. 23, 2012 (5pgs).

EPO Minutes of Oral Proceedings, Jan. 8, 2013 (49 pgs).

EPO Intention to Grant—Rule 71(3) EP, Jan. 11, 2013 (5pgs).

Observations by Third Parties with relevance to European patent application No. 08169413.5, Jan. 22, 2013 (6pgs).

Hult et al., "Dispersion Measurement in Optical Fibers Using Supercontinuum Pulses", Journal of Lightwave Technology, vol. 25, No. 3, Mar. 2007, pp. 820-824.

Wildanger et al., "STED microscopy with a supercontinuum laser source", Jun. 23, 2008 Optics Express, vol. 16, No. 13, pp. 9614-9621.

McConnell et al. "Time-correlated single-photon counting fluorescence lifetime confocal imaging of decayed and sound dental structures with a white-light supercontunuum source", Journal of Microscopy. vol. 225, Pt 2 Feb. 2007, pp. 126-136.

Fiamium Data sheet FemtoPower 1060.

Letter accompanying subsequently filed items, Application No. 08169413.5, Hegner & Partners A/S, Jan. 22, 2013 (1 pg).

EPO Communication from examining division with relevance to European patent application No. 08169413.5, Feb. 19, 2013 (2 pages).

(56) References Cited

OTHER PUBLICATIONS

Annex to the communication from examining division with relevance to European patent application No. 08169413.5, Feb. 19, 2013 (7 pages).
Written submission in preparation for oral proceedings in European patent application No. 08169413.5, Oct. 25, 2012 (28 pages).
Main Auxiliary Request (claims clean) for European patent application No. 08169413.5, Oct. 25, 2012 (6 pages).
Auxiliary Request #1 (claims clean) for European patent application No. 08169413.5, Oct. 25, 2012 (6 pages).
Auxiliary Request #2 (claims) clean for European patent application No. 08169413.5, Oct. 25, 2012 (6 pages).
Auxiliary Request #3 (claims clean) for European patent application No. 08169413.5, Oct. 25, 2012 (6 pages).
Auxiliary Request #4 (claims clean) for European patent application No. 08169413.5, Oct. 25, 2012 (6 pages).
Auxiliary Request #5 (claims clean) for European patent application No. 08169413.5, Oct. 25, 2012 (6 pages).
Auxiliary Request #6 (claims clean) for European patent application No. 08169413.5, Oct. 25, 2012 (6 pages).
Main Auxiliary Request (claims annotated) for European patent application No. 08169413.5, Oct. 25, 2012 (6 pages).
Auxiliary Request #1 (claims annotated) for European patent application No. 08169413.5, Oct. 25, 2012 (6 pages).
Auxiliary Request #2 (claims annotated) for European patent application No. 08169413.5, Oct. 25, 2012 (6 pages).
Auxiliary Request #3 (claims annotated) for European patent application No. 08169413.5, Oct. 25, 2012 (6 pages).
Auxiliary Request #4 (claims annotated) for European patent application No. 08169413.5, Oct. 25, 2012 (6 pages).
Auxiliary Request #5 (claims annotated) for European patent application No. 08169413.5, Oct. 25, 2012 (6 pages).
Auxiliary Request #6 (claims annotated) for European patent application No. 08169413.5, Oct. 25, 2012 (6 pages).
Written Submission for Oral Proceedings, Nov. 21, 2012.
Auxiliary Requests, Nov. 21, 2012.
Reply to Communication from the EPO Exam Division Sep. 2, 2013 (13 pages).
Amended Claims in Main Request clean and annotated versions (10 pages).
Amended Claims in 1st Auxiliary Request clean and annotated versions (10 pages).
Notification of Intention to Grant European patent for EP 08169413, Jan. 8, 2014 (5 pages).
Claims in Main Request in EP 08169413, Jan. 8, 2014 ( 5 pages).
Signatures—Notification of Intention to Grant European patent for EP 08169413, Jan. 8, 2014 (3 pages).
Granted Text of EP Application 08169413.5 (EP 2081074), Jan. 8, 2014 (36 pages).
Communication by telephone EP Application 08169413.5 (EP 2081074), Dec. 20, 2013 (4 pages).
Bibliographic Data EP Application 08169413.5 (EP 2081074), Jan. 8, 2014 (2 pages).
Certificate Grant EP Application 08169413.5 (EP 2081074) (1 page).
Decision to Grant EP Application No. 08169413.5 (EP 2081074), Feb. 6, 2014 (2 pages).

\* cited by examiner

OPTICAL PULSE SOURCES

CROSS-REFERENCE TO RELATED APPLICATIONS

This application claims the benefit of priority under 35 U.S.C. §119 of Great Britain (GB) Patent Application Ser. No. 0800936.7, filed in the United Kingdom on Jan. 19, 2008, which application is incorporated by reference herein.

FIELD OF THE INVENTION

The present invention relates to an optical pulse source, and an illumination source for a Stimulated Emission Depletion (STED) microscope including the optical pulse source.

BACKGROUND ART

Supercontinuum lasers delivering continuous spectra over an ultra-broad bandwidth offer an ideal source for many applications within biomedical imaging, component characterisation, manufacturing control and defense research. The most common form of supercontinuum laser comprises an ultrashort pulse optical pump source operating at a pump wavelength in the Infra-Red (IR) region of the spectrum (typically around 800 nm for a Ti:Sapphire laser or 1064 nm for mode-locked fiber lasers and diode pumped solid-state lasers) and a highly nonlinear photonic crystal fiber, with specially designed dispersion properties. The interaction between the high intensity optical pump pulse and the nonlinear silica fiber causes extreme broadening into the visible and infra red regions of the spectrum to provide spectra spanning from approximately 450 nanometers (nm) to beyond 2.5 micrometer (μm).

The phenomenon of supercontinuum was first proposed in the 1970's by Alfano et al (see R. R. Alfano and S. L. Shapiro, "Observation of self-phase modulation and small-scale filaments in crystals and glasses", Phys. Rev. Lett. 24, 592 (1970)) and in 2000 the first demonstration of a fiber-based supercontinuum made by Ranka and Windelar (see J. K. Ranka et al., "Visible continuum generation in air-silica microstructure optical fibers with anomalous dispersion at 800 nm", Opt. Lett. 25 (1), 25 (2000); see also U.S. Pat. No. 6,097,870) using a Ti:Sapphire mode-locked femtosecond laser 10 to pump a photonic crystal fiber 11 with zero dispersion wavelength at approximately 760 nm in free space through launch optics 12 as shown in FIG. 1. More recently, researchers and companies have utilized nanosecond and picosecond-based pump sources operable at around 1064 nm wavelength to pump photonic crystal fibers with a zero dispersion wavelength close to 1 μm to generate high brightness supercontinuum products.

Commercial supercontinuum products, such as Fianium Limited's supercontinuum fiber laser model no. SC450, rely on mode-locked fiber oscillators and high-power optical fiber amplifiers to generate highly intense pulses at the pump wavelength, which when injected into a nonlinear photonic crystal fiber (PCF), result in extreme spectral broadening into both the visible and IR regions of the spectrum.

FIG. 2 shows an example of such a system, where a mode-locked fiber oscillator 21 produces low energy optical pulses of approximately 10 picoseconds (ps) duration and at a repetition rate of 20 MHz to 100 MHz. The pulses are amplified within a cascaded fiber amplifier 22, comprising one or more stages of amplification, with optical isolation 23 between each stage. The output of the amplifier is a high-energy pulse of up to 400 nJ and tens of kilowatts peak power. The output of the amplifier is injected into a length of highly nonlinear photonic crystal fiber (PCF) 24 with anomalous dispersion at the pump wavelength (1064 nm) and zero dispersion at a wavelength close to the pump wavelength. The spectral bandwidth of the pulse broadens within the PCF, creating a pulse of approximately 100 nJ energy and a bandwidth from 400 nm to 2.5 μm that exits the PCF 24.

The pulsed nature of these sources and high repetition rates (20 MHz to 160 MHz), makes these sources attractive to both applications requiring quasi-continuous wave radiation as well as applications involving time-resolved measurements such as FLIM (Fluorescent lifetime imaging) and TCSPC (time correlated single photon counting). However, often, the high repetition rates can be a limiting factor in lifetime imaging, where the pulse-to-pulse separation (50 ns for a 20 MHz source, down to a few nanoseconds for a 160 MHz source) can be much shorter than the lifetime of the sample under evaluation. In this event, one requires a lower pulse repetition rate.

In general, most mode-locked laser systems operate at pulse repetition rates of several tens of MHz (diode-pumped solid-state (DPSS) lasers typically operate from 80 MHz to 100 MHz, and fiber lasers from 20 MHz to several hundreds of MHz). Some applications require lower repetition rates— for example fluorescent-imaging lifetime microscopy (FLIM), where fluorescent-labeled molecules are excited by an incident optical pulse and the decay of the fluorescence is monitored before the next optical pulse arrives. In FLIM, the lifetimes of interest can very often exceed tens or even hundreds of nanoseconds, and therefore it is often required to have repetition rates of 40 MHz and below. Repetition rates of less than 20 MHz, while not impossible to achieve, are difficult to deliver from a mode-locked fiber oscillator due to high nonlinearity within a long cavity (10 m for a 10 MHz oscillator). From a DPSS source, such a cavity (5 m long for 20 MHz and 100 m in length for 1 MHz) is almost impossible to make due to the required complexity of the cavity design.

SUMMARY OF THE INVENTION

According to a first aspect of the invention there is provided an optical pulse source comprising an optical pump laser operable to generate optical pump pulses at a pump pulse repetition rate. The source also includes a nonlinear optical element, and a gating device provided between the pump laser output and the nonlinear optical element. The gating device is operable to selectively control the launch of pump pulses into the nonlinear optical element at a variable, lower repetition rate, to thereby selectively control the generation of optical supercontinuum pulses within the nonlinear optical element and their repetition rate.

The optical pulse source enables optical supercontiuum pulses to be generated with flexible control of the output pulse repetition rate, and thus the pulse-to-pulse separation. Control of the inter-pulse separation is of particular advantage where the source is used to provide supercontinuum illumination in applications where decay lifetimes are measured, such as FLIM, and the optical pulse source can be operated to generate supercontiuum pulses at pulse repetition rates of less than 20 MHz for such applications.

The nonlinear optical element may comprise one or more nonlinear optical crystals, such as lithium triborate (LBO), barium borate (BBO), cesium lithium borate (CLBO), periodically poled lithium niobate (PPLN) or periodically poled potassium titanyl phosphate (PPKTP) or a microstructured optical fiber, which is preferably one of a highly non-linear photonic crystal fiber, a side-hole fiber, a hollow-core photonic bandgap fiber and a solid-core photonic bandgap fiber.

The optical pump laser may comprise a mode-locked laser. The pump pulse repetition rate may be variable. The optical pump laser may alternatively comprise a modelocked fiber oscillator operable to generate optical pump pulses. The optical pulse source preferably further comprises an optical fiber amplifier configured to receive pump pulses from the modelocked fiber oscillator and operable to amplify the pump pulses. The modelocked fiber oscillator and the amplifier together form a master oscillator power amplifier (MOPA). The gating device may be provided between the modelocked fiber oscillator and the optical fiber amplifier.

The gating device preferably comprises an optical modulator element, such as an acousto-optic modulator, an electro-optic modulator or a semiconductor saturable absorber mirror (SESAM) modulator. The modulator element is preferably synchronised with the output of the optical pump laser, to selectively control the repetition rate of pulses launched into the fiber, to thereby selectively control the output pulse repetition rate. The gating device is preferably operable to control the output pulse repetition rate from a few Hertz up to 100 MHz.

The optical pulse source preferably further comprises a wavelength-tunable optical bandpass filter configured to receive an optical supercontinuum pulse and to wavelength filter the pulse at a predetermined wavelength. The wavelength-tunable optical bandpass filter is preferably configured to receive a plurality of optical supercontinuum pulses in a pulse set and to wavelength filter each pulse at a respective one of a corresponding plurality of predetermined wavelengths, to thereby form a wavelength-interleaved optical supercontinuum pulse set. The wavelength-tunable optical bandpass filter is preferably configured to filter a plurality of such pulse sets in series to thereby form a repeating wavelength-interleaved optical continuum pulse train.

The transmission spectrum of the wavelength-tunable optical filter can be selected to pass any wavelength or set of wavelengths within the supercontinuum spectrum, to thereby control the spectral profile of each output optical pulse. The optical pulse source can thus be used as an optical source for Pulse Interleave Excitation Forster Resonance Energy Transfer (PIE-FRET).

The optical pulse source preferably further comprises second gating device provided after the nonlinear optical element and configured to pulse-pick received optical continuum pulses to a lower pulse repetition rate. The second gating device preferably comprises an acousto-optical modulator or a wavelength-tunable optical bandpass filter. The wavelength-tunable optical bandpass filter is preferably an acousto-optic tunable filter.

Preferably, a single wavelength-tunable optical bandpass filter is configured to perform both wavelength filtering and pulse-picking. The second gating device is preferably further operable to reduce the optical intensity of one or more optical pulses in the pulse set or train. The second gating device can thereby be operated to control the optical intensity of the pulses in a train of optical pulses of different wavelengths, so that the optical intensity can be changed for pulses of different wavelengths.

The optical pulse source may alternatively further comprise: an optical beam splitter coupled to the output of the optical supercontinuum pulse source, to thereby split the optical supercontinuum pulses into first and second split pulses in first and second optical paths; first and second optical filters having different wavelength transmission spectra respectively provided in the first and second optical paths; an optical delay element provided in the first optical path; and an optical beam combiner arranged to recombine the first and second split pulses from the first and second optical paths into pulse train in a common optical path. A pulse train comprising interleaved optical supercontinuum pulses of two different wavelengths is thereby produced.

According to a second aspect of the present invention there is provided a method of scaling the energy of optical supercontinuum pulses generated using the optical pulse source as described above. The method comprises the steps of: reducing the pump pulse repetition rate of the optical pump laser; and increasing the pump pulse duration. This invention therefore enables the development of higher-energy supercontinuum pulse sources for certain applications where higher pulse intensity is required, with STED microscopy being one example.

The method may comprise reducing the pump pulse repetition rate to less than 20 MHz and increasing the pump pulse duration to greater than 10 ps, and most preferably to at least 200 ps.

According to a third aspect of the present invention there is provided an illumination source for stimulated emission depletion microscopy. The illumination source comprises an optical pulse source as described above, configured to generate output optical pulses having a repetition rate in the range 1 MHz to 10 MHz and an energy spectral density of at least 100 picojoules per nanometer (pJ/nm), the optical pulse source being operated to scale the energy of the optical supercontinuum pulses by reducing the pump pulse repetition rate of the optical pump laser and increasing the pump pulse duration.

The optical pulse source may be operated to reduce the pump pulse repetition rate to less than 20 MHz. The optical pump laser is preferably operable to generate optical pump pulses having a pump pulse duration of greater than 10 ps, and most preferably at least 200 ps.

According to a fourth aspect of the present invention there is provided an optical fluorescence microscope based on stimulated emission and depletion. The microscope comprises an illumination source as described above, with the illumination source being configured to provide both excitation illumination and stimulated emission illumination.

In conventional STED microscopes (see, e.g., G. Donnert et al., Proceedings of the Natural Academic Society U.S.A 103, 11440-11445 (2006)) two lasers are used simultaneously, one (typically a Ti:Sapphire laser) with high optical intensity to form the STED beam and a second tunable visible laser to excite the fluorescence. Conventional supercontinuum lasers, based on modelocked fiber laser-pumped PCF's or Ti:Sapphire laser-pumped PCF's, are too low in pulse energy for STED. Using a reduced repetition rate and longer pulse according to the present invention, an optical pulse source is provided which is operable to generate supercontinuum pulses having a pulse energy spectral density approaching 1 nJ/nm, making this a suitable single-source solution for both fluorescence excitation and STED within a STED microscope.

Another benefit of this invention is that it provides the ability to be flexible in pump pulse duration and the length of microstructure optical fiber required to generate the supercontinuum output pulses.

The cases described within this invention relate specifically, but not exclusively to, the wavelengths falling within the gain bandwidth of Ytterbium doped silica fibers—between 1020 nm and 1080 nm. Equally, this invention can relate to supercontinuum pulses generated using a Nd-doped fiber laser or Er-doped fiber laser or DPSS laser source as the optical pump laser.

BRIEF DESCRIPTION OF THE DRAWINGS

The preferred embodiments of the present invention will now be described by way of example only and with reference to the accompanying drawings in which.

DETAILED DESCRIPTION OF THE INVENTION

Figure 3:
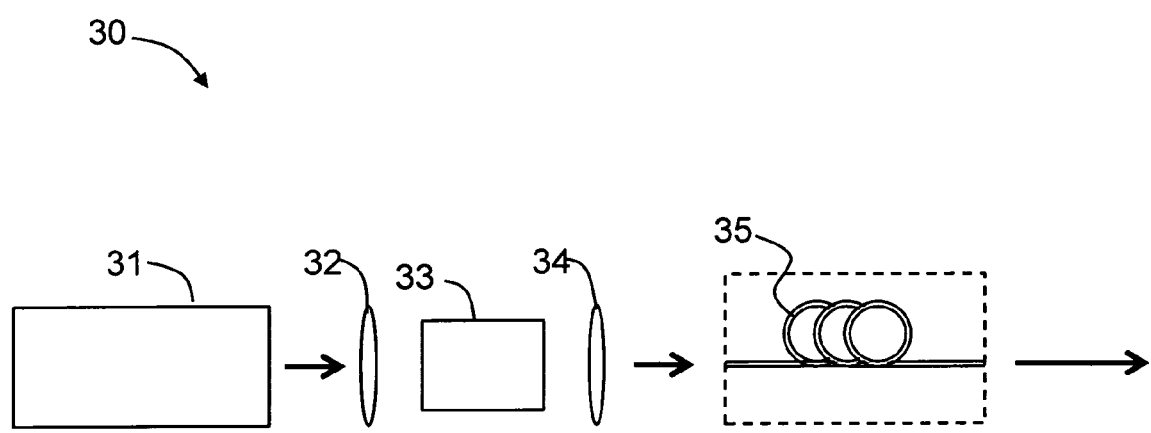
FIG. 3 is a schematic illustration of an optical pulse source according to a first embodiment of the present invention generated from a free-space DPSS mode-locked laser source.

Referring to FIG. 3, a first embodiment of the invention provides an optical pulse source 30 comprising an optical pump laser source 31, a microstructured optical fiber 35 and a gating device 33 (also referred to below as "gating means" 33).

The optical pump laser 31 in this example takes the form of a diode pumped solid state (DPSS) laser source (for example a mode-locked 1064 nm laser operating at 76 MHz), which is operable to produce pulses of approximately 200 nJ energy and duration 10 ps. The output pulses from the pump laser 31 pass through lens (e.g., a set of lenses) 32 to the gating means 33, which here comprises an optical modulator, synchronised to the pump laser 31 and operable so that it can gate the pump pulses and produce a pulse train having a reduced repetition rate (Rr), where Rr=Rf/N, where Rf is the pump laser fundamental frequency (in this example 76 MHz) and N is a positive integer. The pulses output from the modulator gating device 33 are injected via optics 34 into the microstructured fiber 35, which here comprises a nonlinear element such as a photonic crystal fiber (PCF). Propagation through the PCF 35 causes the pulses to broaden spectrally to produce supercontinuum pulses at the reduced, output pulse, repetition rate Rr. FIG. 3 thus illustrates a low repetition rate picosecond or femtosecond supercontinuum pulse source, in this case pumped from a free-space DPSS mode-locked laser source.

Figure 1:
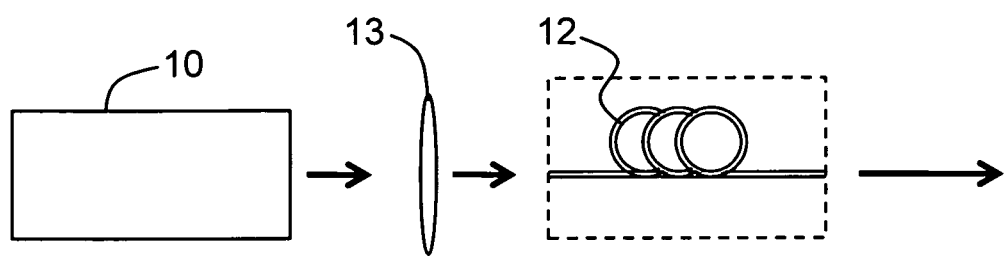
FIG. 1 is a schematic illustration of a prior art arrangement for the generation of an optical supercontinuum.
Figure 2:
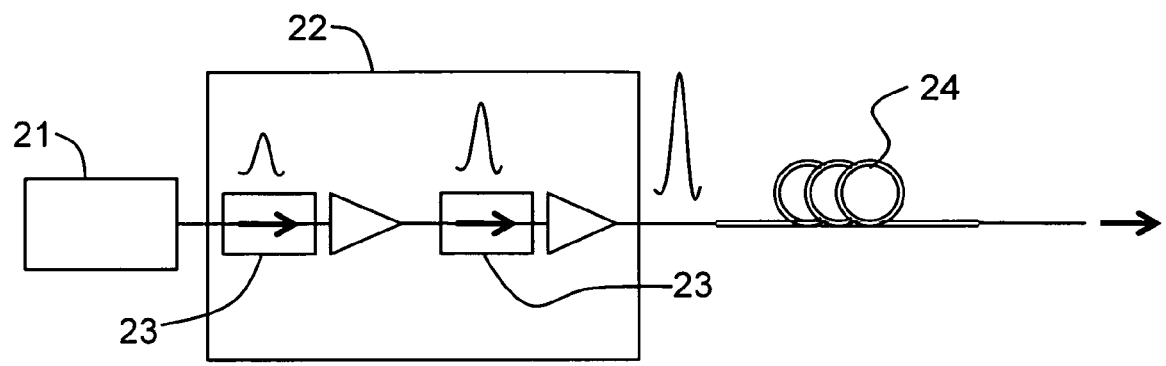
FIG. 2 is schematic illustration of a prior art supercontinuum fiber laser.
Figure 4:
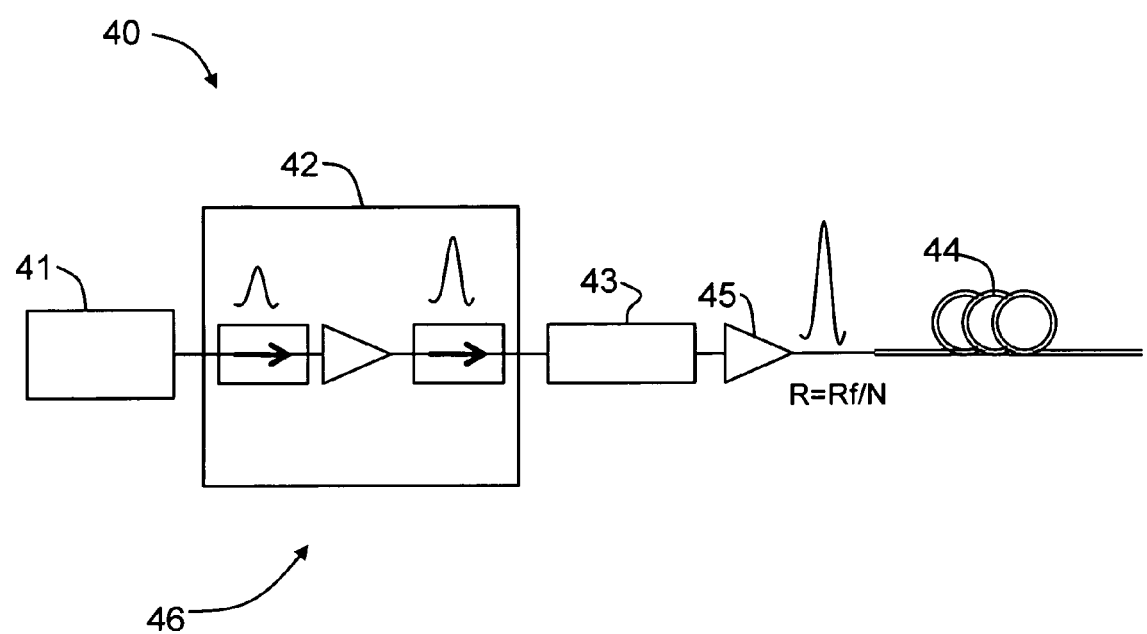
FIG. 4 is a schematic illustration of an optical pulse source according to a second, embodiment of the present invention.

One of the major drawbacks with the use of free-space optics, as shown in FIG. 3, is that launch stability into the small structures of nonlinear PCF's is poor and the end face of these fibers can easily be damaged. FIG. 4 shows an optical supercontinuum pulse source 40 according to a second, all fiber embodiment of the invention, similar to the arrangement shown in FIG. 2. The optical pump laser 41 comprises in this example a mode-locked fiber oscillator operable at a repetition rate Rf of 40 MHz to produce low energy pulses at 1064 nm and having a pulse duration of approximately 10 ps. The pump pulses are amplified in an optical fiber amplifier 42. The pump pulses are then injected into gating device 43, which in this example is in the form of a fiber-coupled modulator, which in this example comprises an acousto-optic modulator (AOM). It will be appreciated by one skilled in the art that an Electro-Optic Modulator (EOM), SESAM modulator or any other type of fast modulation device, capable of switching with rise times of less than one microsecond may alternatively be used. The modulator gating means 43 is synchronized to the oscillator frequency (Rf) and is operable to gate the oscillator output, i.e. the pump pulses, down to a repetition rate of a few tens of KHz, and hence pulse-pick the pump pulses, thereby providing a selectable pump pulse frequency Rr=Rf/N (N is a positive integer value).

The reduced repetition rate pump pulses outputted from the modulator gating means 43 are amplified in a power amplifier 45. The pump laser 41 and the power amplifier 45 together form a master oscillator power amplifier (MOPA) 46. The pump pulses output from the MOPA 46 have a maximum pulse peak power, governed by the nonlinear limitations of the power amplifier 45 of, for example, approximately 40 KW, corresponding to a pump pulse energy of approximately 400 nJ.

Following amplification, the pump pulses are input into a length of highly nonlinear microstructured optical fiber 44, in this example PCF, with a zero dispersion wavelength at approximately 1040 nm. Propagation through the PCF 44 produces extensive spectral broadening of the pump pulses into the visible and further out into the IR region of the spectrum, thereby forming supercontinuum pulses. The supercontinuum pulses have a supercontinuum spanning from below 450 nm to greater than 2000 nm, a total supercontinuum pulse energy of approximately 100 nJ, and energy spectral density of approximately 50 picoJoules/nm (pJ/nm).

In this example, since the oscillator remains the same, for a given output pulse energy one achieves nominally identical spectra for all repetition rates. The pulse energy is fixed and clamped, but the pulse to pulse separation increased with reducing repetition rate.

In an alternative arrangement, the optical pulse source 40 of this embodiment may be operated with the low-power mode-locked fiber oscillator (pump laser) 41 generating pulses having a pulse duration of 200 ps. Amplification within a fiber amplifier with nonlinear clamp on the peak power of approximately 40 KW, results in a corresponding maximum pump pulse energy of 8 µJ (for example, 1 MHz, 8 W average power and 200 ps pulse duration). Supercontinuum pulses having a total supercontinuum pulse energy of approximately 2 µJ and energy spectral density of approximately 1 nJ/nm are produced.

Figure 5:
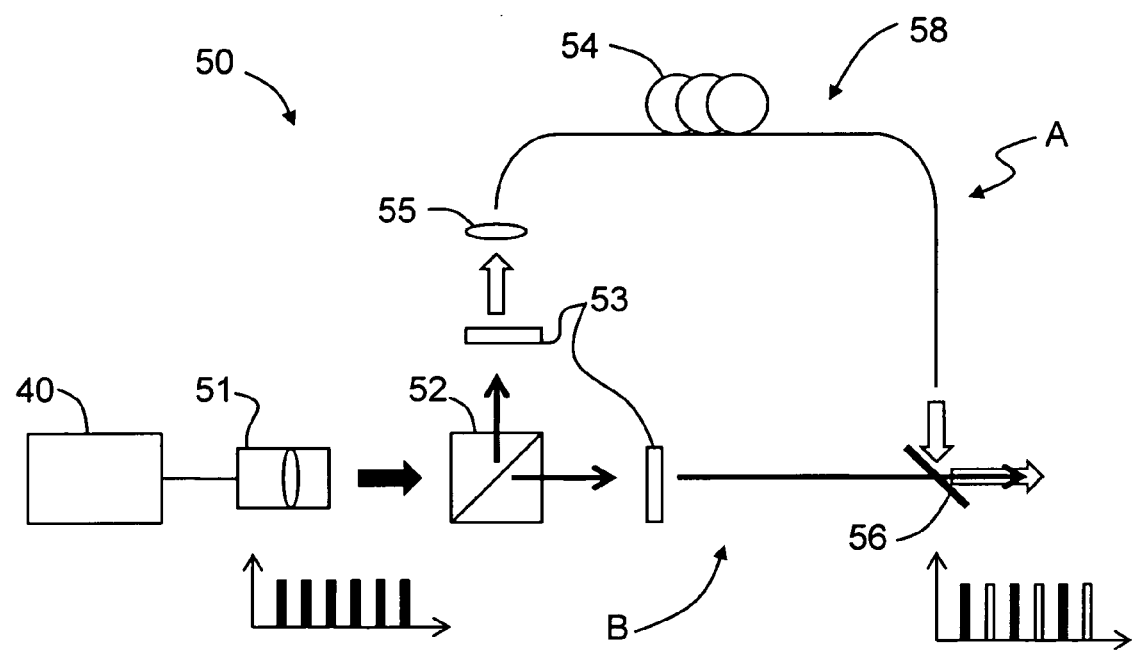
FIG. 5 is a schematic illustration of an optical pulse source according to a third embodiment of the present invention.

Referring to FIG. 5, a third embodiment of the invention provides an optical pulse source 50 which adds to the optical pulse source 40 according to the second embodiment. In this embodiment, the optical pulse source 50 further comprises a polarizing beam splitter 52 (a non-polarizing beam splitter or other similar splitting mechanism may alternatively be used), optical filters 53, an optical delay element 54, and a beam combiner 56. The output of the optical pulse source 40 (see also leftmost inset pulse plot) is passed through optics 51 and is thereafter split into two beam paths (A, B) by the beam splitter 52. The optical filters 53 are provided in each of the split beam paths. The optical filters 53 may be acousto-optic tunable filters (AOTF), each being operable to transmit a different wavelength, or standard filters of different transmission wavelengths.

The optical delay element 54, which takes the form of an optical fiber delay line, is provided in one beam path (A). For a 20 MHz optical supercontinuum pulse repetition rate output from the optical pulse source 40, a delay of 25 ns is required for the pulses travelling along path A. The optical fiber delay line 54 thus comprises a delay path of between 5 m and 7.5 m in length. A coupling lens 55 is provided for launching the split pulses into the delay line 54. Propagation along path A causes the split optical pulses in that path to be delayed with respect to the optical pulses in the other split beam path (B). It will be appreciated that this can alternatively be achieved in free-space.

The beam combiner 56, which as shown comprises a dichroic mirror but may alternatively comprise a fiber-coupler, is provided at the ends of the split beam paths A and B to recombine the two split pulse trains, to thereby form a pulse train comprising interleaved pulses of two different wavelengths, as represented by the white and black arrows (see also rightmost inset pulse plot). Although an optical fiber delay line 54 is the preferred choice, this requires launching of the light into an optical fiber 54 by a suitable lens 55, incurring additional loss and instability. This approach is attractive as an experiment, but is less practical for a commercial instrument. In addition, this approach cannot use a variable supercontiuum pulse repetition rate, since the required path imbalance, introduced by the delay line, changes with repetition rate.

Figure 6:
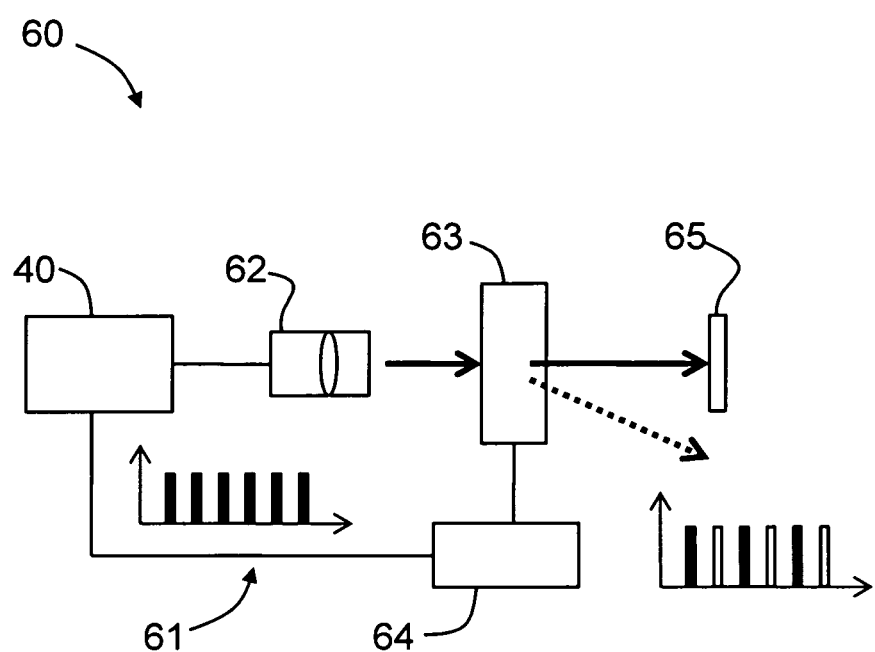
FIG. 6 is a schematic illustration of an optical pulse source according to a fourth embodiment of the present invention.

A fourth embodiment of the invention provides an optical pulse source 60, as shown in FIG. 6, comprising an optical pulse source 40 according to the second embodiment and a wavelength-tunable optical bandpass filter 63. The optical pulse source 40 is operable to generate optical supercontinuum pulses having wavelength spectra from 400 nm to 2000 nm, at pulse repetition rates, variable between 40 MHz and less than 100 kHz. The optical pulse source 40 is provided with an on-board micro-processor controller, which determines when the supercontinuum pulses are delivered, and provides a transistor-transistor logic (TTL) output trigger signal. The optical output of the optical pulse source 40 is in free space, and the beam is collimated or waisted by optics 62.

In an example embodiment, the wavelength-tunable optical bandpass filter 63 comprises an acousto-optic tunable filter (AOTF) driven by an RF driver or Direct Digital Synthesiser (DDS) 64. The AOTF 63 is operable over a spectral range (for example from 400 nm to 700 nm) covered by the optical supercontinuum pulse spectrum. The DDS 63 is synchronised with the optical pulse source 40 either through an external trigger 61, or from a microprocessor, such that the AOTF can be modulated at the operating frequency of the optical pulse source 40 or at any lower frequency. The AOTF 63 can also be operated in burst mode, to transmit a burst of optical pulses.

By changing the RF frequency of the AOTF driver 64, one can tune the filter output to any wavelength lying within the AOTF 63 and supercontinuum spectral ranges. Typical AOTF's have spectral ranges of, for example, from 400 nm to 700 nm in the visible region, from 700 nm to 1100 nm in the near infra-red (NIR) and from 1100 nm to 2000 nm in the IR. All of these wavelengths are available within the spectrum of the supercontinuum optical pulses generated by the optical pulse source 40.

The first order diffracted output of the AOTF 63 forms the output of the optical pulse source 60, and may be launched into an optical fiber or used in free space. The zero-order of the AOTF, is either absorbed by a suitable beam dump 65 or can form a second output of the optical pulse source 60. In this example, the AOTF 63 is triggered to operate at one user-defined wavelength for one pulse and a second user defined wavelength for the next pulse, thus generating a wavelength-interleaved output pulse train of alternating wavelength pulses, as shown in the rightmost inset pulse plot. The optical pulse source 60 is therefore suitable for use as an illumination source for PIE-FRET.

Figure 7A:
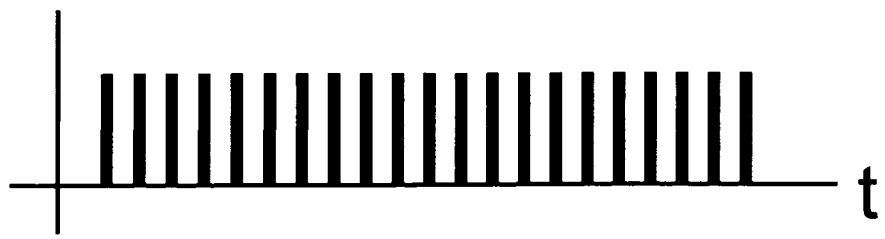
FIG. 7A and FIG. 7B are representations of a first set of output optical pulse trains exiting the microstructured optical fiber (FIG. 7A) and exiting the AOTF (FIG. 7B), which may be generated by the optical pulse source of FIG. 6.
Figure 7B:
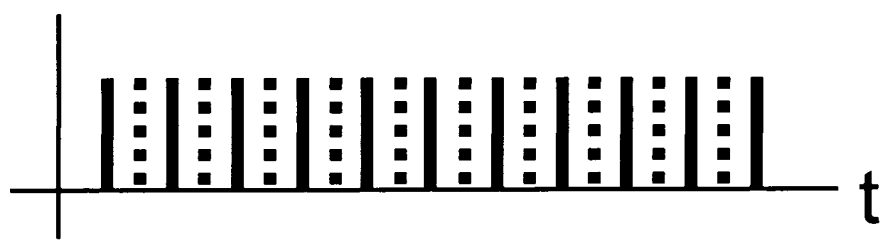

Dependent on the speed of the AOTF 63 (which is often limited by the spot size of the beam through the crystal), the AOTF can be configured to deliver pulses at the optical supercontinuum pulse repetition rate, as shown in FIG. 7A and FIG. 7B, where FIG. 7A shows the pulses from the optical pulse source 40 and FIG. 7B shows the AOTF output, i.e. the output of the optical pulse source 60, which comprises a wavelength-interleaved train of filtered pulses at two different wavelengths (represented by the solid and dashed lines).

Figure 8A:
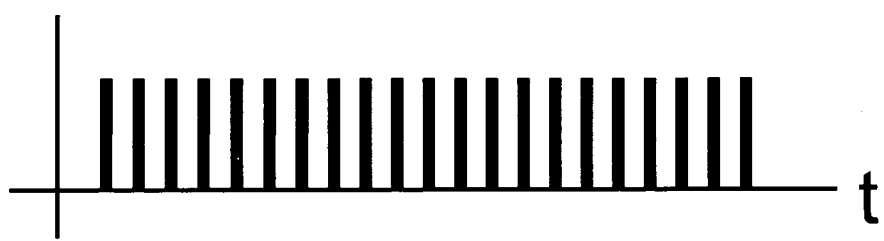
FIG. 8A and FIG. 8B are representations of a second set of output optical pulse trains exiting the microstructured optical fiber (FIG. 8A) and exiting the AOTF (FIG. 8B), which may be generated by the optical pulse source of FIG. 6.
Figure 8B:
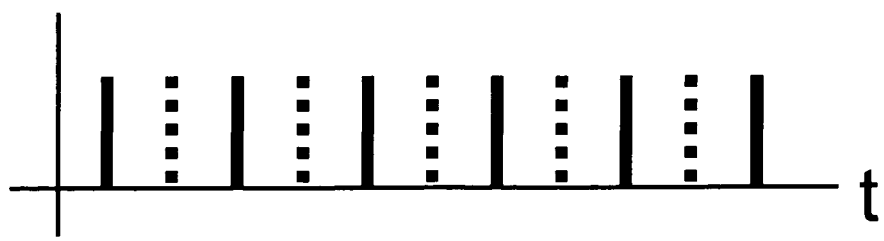

The AOTF 63 may additionally be operable as a pulse-picker (i.e., a gating device) to reduce the pulse repetition rate for the optical supercontinuum output pulses. As shown in FIG. 8A and FIG. 8B, the supercontinuum pulse train is shown in FIG. 8A, and the AOTF output pulse train of wavelength filtered and reduced repetition rate pulses at two different wavelengths (represented by the solid and dashed lines) is shown in FIG. 8B.

Figure 9A:
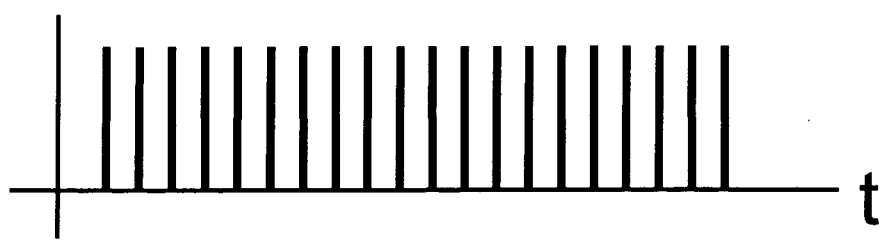
FIG. 9A and FIG. 9B are representations of a third set of output optical pulse trains exiting the microstructured optical fiber (FIG. 9A) and exiting the AOTF (FIG. 9B), which may be generated by the optical pulse source of FIG. 6.
Figure 9B:
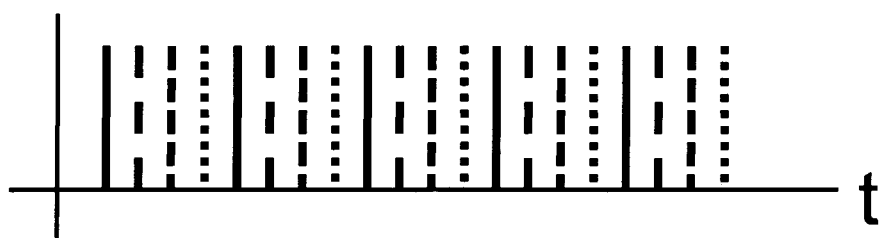

The AOTF 63 is operable to filter the supercontinuum optical pulses at more than two wavelengths, to produce a very complex pulse train which might have numerous applications within advanced imaging applications. FIG. 9A and FIG. 9B, for example, show the supercontinuum optical pulses (FIG. 9A) at a given repetition rate, and an output optical pulse train from the optical pulse source 60 (FIG. 9B) with the AOTF 63 operating to filter each set of four supercontinuum pulses at four different wavelengths, to thereby generate an output optical pulse train comprising interleaved optical pulses of four different wavelengths, as represented by the four different line types in the plot.

The AOTF 63 is also operable to amplitude control the output pulse intensities, which provides another degree of flexibility in optimising system performance. This could, for example, balance the illumination intensities for optical pulses at different wavelengths to pre-compensate for different fluorescence levels from donor and acceptor fluorophores in FRET.

The combination of the variable optical supercontinuum pulse repetition rate and AOTF to form a variable repetition rate and wavelength optical pulse source, means that one can produce a series of repetition rates and with arbitrary, wavelength varying pulse trains. It will be appreciated that the described variable repetition rate optical pulse source may be replaced by a fixed repetition rate optical pulse source generating supercontinuum pulses, provided that the AOTF can operate sufficiently fast. For example, it is difficult to produce modelocked lasers at repetition rates much below 20 MHz, and this would require a switching speed of the AOTF to be of the order of 10 ns, to reliably switch between colours with good extinction ratio between adjacent pulses—essential for FRET applications where very sensitive electronics and detectors are used.

Typically, switching speeds of the 100 ns to microsecond level are achievable with AOTF's, meaning that an optical pulse repetition rate of 5 MHz and below becomes a realistic solution. The variable repetition rate optical pulse source presents a means to achieving this speed, and also provides the flexibility to further vary the repetition frequency.

An example in which the optical pulse source 60 may be used as an illumination source, is in an imaging application known as pulsed-interleaved-excitation, most commonly used within FRET (Forster Resonance Energy Transfer). FRET is the radiation-less energy transfer from an optically excited donor fluorophore to a nearby acceptor molecule through dipole-dipole interaction, and enables quantitative length measurement due to the strong distance dependence of FRET. In conventional FRET, the quality of measurement is hampered by incomplete FRET pairs (having a missing or non-functional acceptor molecule), which look very similar to FRET pairs with large donor-acceptor distances. In addition, determination of the FRET efficiency requires quantitative information on the detection efficiency for donor and acceptor fluorescence—including spectral crosstalk.

Pulse interleave excitation FRET (PIE-FRET) overcomes these issues by having consecutive pulses operating at different wavelengths. The first pulse operates at a wavelength to excite a donor molecule and initiate FRET. This leads to donor-to-acceptor fluorescence. The second pulse operates at a wavelength to excite directly the acceptor fluorophore but not the donor. This process determines whether or not the FRET pair has a properly functioning acceptor. PIE-FRET has been demonstrated using two different colour laser diodes, modulated at the same frequency but with one diode delayed in time with respect to the other, producing a pulse train of alternating colour pulses. Typically, this process is carried out at fairly high repetition rates (20 MHz, to 40 MHz) with pulse-to-pulse time separations of the order of 50 ns to 25 ns respectively, which is usually acceptable for measurement of most biological lifetimes, and provides high throughput for building up large images. The restriction of the two diode approach is that the wavelengths are limited to those available from suitable laser diodes. The optical pulse source 60 of the present invention allows the production of pulse trains having a combination of any sets of wavelengths within the supercontinuum spectral range.

In a fifth embodiment of the invention, the use of a fiber laser incorporating a pulse-picker element allows for the delivery of higher energy supercontinuum lasers within the visible region of the spectrum.

In some examples, it is important to be able to scale the energy from the supercontinuum optical pulses—particularly within the visible region of the spectrum. Using the same system configuration as FIG. 4, it is possible to scale the average supercontinuum energy by reducing the pump pulse repetition rate but increasing the pump pulse duration to hundreds of picoseconds. This effectively results in a higher energy 1064 nm fundamental input pulse (the peak power of the pulse is limited within the fiber amplifier by nonlinear interactions dominated by stimulated Raman scattering (SRS)) and a corresponding increase in the average output supercontinuum pulse energy across the supercontinuum spectra exiting the PCF.

By increasing the pulse duration, one therefore increases the average pulse energy attainable within the SRS limit of the fiber amplifier. The result, after injection into the PCF, is an increase in the resulting spectral energy density of the supercontinuum pulses. For example, a standard supercontinuum laser operating at 20 MHz repetition rate and delivering 2 W average power in the supercontinuum, produces a supercontinuum pulse energy of approximately 100 nJ. When the visible region of this source output is filtered, the average spectral energy density is in the region of 50 pJ/nm (400 mW over a 400 nm bandwidth).

In known commercial supercontinuum fiber lasers, such as the aforementioned SC450 from Fianium Ltd., or the SuperK from Koheras A/S, the average energy spectral density of pulses within the visible region of the spectrum ranges from approximately 35 pJ/nm (SuperK Rapid, 3 mW/nm at 80 MHz) to 50 pJ/nm (SC450, 1 mW/nm at 20 MHz). For these sources, the total supercontinuum power ranges from 2 W to 6 W and is generated using pulsed optical pump sources of between 8 W and 20 W average power. The spectral broadening in the photonic crystal fiber is generated by the high peak power of the pump source optical pulses which can be as high as 40 KW (8 W, 20 MHz, 10 ps). As an example, a typical SC450-2 supercontinuum laser from Fianium Ltd., with a power spectral density in the visible of 1 mW/nm, has an energy spectral density of approximately 50 pJ/nm ($50 \times 10^{-12}$ J/nm), and is pumped by a pulsed optical pump source operating at 20 MHz with a pulse duration of approximately 10 ps and an output power of approximately 8 W.

In order to scale the energy spectral density of these know supercontinuum sources at these repetition rates to 500 pJ/nm, pump laser source having between 10 and 15 times the output power would be required, equating to a pulse optical pump source with average power of between 80 W and 285 W.

In this embodiment, a pulse-picked optical pulse source 40, as shown in FIG. 6, operating at a 5 MHz pulse repetition rate and a 10 m length of PCF 44, achieves the same visible power and spectral bandwidth but this results in a 5-Fold increase in spectral energy to 200 pJ/nm. Starting with a 200 ps optical pulse and a standard length of nonlinear fiber, it is possible to scale the spectral energy density to in excess of 1 nJ/nm at 1 MHz, with an average visible power of approximately 400 mW (over a 400 nm band) at 1 MHz.

A sixth embodiment of the invention comprises a pulse-picked optical pulse source 40, as shown in FIG. 6, in which the pump pulse repetition rate is reduced to 1 MHz, and the pulse duration increased to approximately 200 ps. In order to generate the required spectral broadening within the PCF 44, 40 KW of pulse peak power is attained from the pulsed pump source 41 at an average output power of 8 W, resulting in a 2 W supercontinuum, with 1 mW/nm power spectral density in the visible spectral region, corresponding to approximately 1 nJ/nm energy spectral density.

A seventh embodiment of the invention provides a method of scaling the energy of optical supercontinuum pulses generated using the optical pulse sources 30 or 40 of the previously described example embodiments. The method comprises reducing the pump pulse repetition rate of the optical pump laser 31 or 41 and increasing the pump pulse duration.

In general, the magnitude of spectral broadening of an optical source propagating through a given nonlinear optical element is directly proportional to the intensity of that source. For a pulsed laser source, the intensity is given by the pulse peak power:

$$P_{peak} = P_{avg}/(R \ast dT)$$

where $P_{peak}$ is the peak power of the pulse, $P_{avg}$ is the average power of the laser source, R is the pulse repetition frequency of the source and dT is the temporal duration of the pulse. The energy of the pulse is given by:

$$E = P_{avg}/R.$$

For a laser based on a MOPA (Master Oscillator, Power Amplifier) design, while the average power of the laser can be scaled, the peak power is limited by nonlinear effects (mainly stimulated Raman scattering) within the fiber amplifier system, which has the effect of clamping the peak power, resulting in:

$$P_{peak} = \text{Constant} = P_{avg}/(R \ast dT).$$

The method realises that, to a first approximation, the extent of spectral broadening within a pulsed supercontinuum fiber laser can be considered to be limited by the peak power of the pulse, but that the energy of the pulse can be changed by adjusting the pulse repetition rate and the temporal duration of the pulse.

The maximum pulse energy of the optical pulse source 30 and 40, and hence the maximum pulse energy (or energy spectral density) of resulting supercontinuum pulses, can therefore be increased by reducing the pulse repetition rate of the pump laser 31 and 46 and, in the case of the MOPA 46 by either reducing the pulse repetition rate or scaling the average power from the amplifier 45. For a given amplifier design and average power output, an increase in pulse energy can be achieved with a reduction of pump pulse repetition rate and increase of pump pulse duration.

The limit of peak power extractable from a given fiber amplifier is determined by the length of the amplifier fiber and the cross sectional area of the mode propagating within this fiber. For standard single mode optical fibers operating at 1 μm, the peak power limit can be as low as a few kW, but this can be scaled to tens of kW for large mode area (LMA) fibers where the effective mode field diameter within the fiber mode can be greater than 12 μm.

The described embodiments make use of the reduction in pulse repetition rate to enable scaling of the energy spectral density of the supercontinuum without the requirement for scaling the power spectral density and therefore the average power from the pulsed optical pump source.

From the foregoing therefore, it is evident that the present invention enables the delivery of supercontinuum spectra or filtered visible laser sources at a range of pulse repetition rates from 100 MHz down to a few Hz or less. This invention has clear benefits over conventional supercontinuum sources for applications where the pulse-to-pulse separation of the source is an important parameter.

Various modifications may be made without departing from the scope of the present invention. For example, where the DPSS pump laser may be replaced by a different type of mode-locked laser, and may comprise a MOPA. The PCF may be replaced by a different micro-structured optical fiber, such as a side-hole fiber, hollow-core photonic bandgap fiber or solid-core photonic bandgap fiber, or may be replaced by a different nonlinear optical element, such as a nonlinear crystal like such as LBO, BBO, CLBO, PPLN, PPKTP or any other nonlinear optical crystal phase matched to produce frequency conversion of the pump laser output. Also, in the embodiments of the invention comprising a MOPA, the gating device may alternatively be located after the power amplifier.

What is claimed is:

1. An optical pulse source for generating optical supercontinuum pulses at a repetition rate, comprising:
    an optical pump laser operable to generate a number of optical pump pulses at a pump pulse repetition rate;
    a nonlinear optical element arranged to receive the optical pump pulses and configured to generate therefrom optical supercontinuum pulses;
    a gating device provided between the pump laser and the nonlinear optical element and operable to selectively limit the number of optical pump pulses received by the nonlinear optical element in order to generate optical supercontinuum pulses at a user selectable repetition rate lower than the pump pulse repetition rate; and
    wherein said optical supercontinuum pulses have a supercontinuum spanning from below 450 nm to greater than 2000 nm.

2. An optical pulse source according to claim 1, wherein the nonlinear optical element comprises a nonlinear optical crystal or a microstructured optical fiber.

3. An optical pulse source according to claim 2, wherein the microstructured optical fiber comprises a highly non-linear photonic crystal fiber, a side-hole fiber, a hollow-core photonic bandgap fiber, or a solid-core photonic bandgap fiber.

4. An optical pulse source according to claim 1, wherein the optical pump laser comprises a mode-locked laser or a mode-locked fiber oscillator.

5. An optical pulse source according to claim 4, wherein the optical pulse source further comprises an optical fiber amplifier configured to receive pump pulses from the modelocked fiber oscillator and is operable to amplify the pump pulses and wherein the gating device is provided between the modelocked fiber oscillator and the optical fiber amplifier.

6. An optical pulse source according to claim 1, wherein the gating device comprises an optical modulator element, an acousto-optic modulator, an electro-optic modulator, or a semiconductor saturable absorber mirror (SESAM) modulator.

7. An optical pulse source according to claim 1, wherein the optical pulse source further comprises a wavelength-tunable optical bandpass filter configured to receive at least one optical supercontinuum pulse and to wavelength filter the at least one optical supercontinuum pulse at a predetermined wavelength.

8. An optical pulse source according to claim 7, wherein the wavelength-tunable optical bandpass filter is configured to receive a plurality of optical supercontinuum pulses in a pulse set, and to wavelength filter each pulse at a respective one of a corresponding plurality of predetermined wavelengths, to thereby form a wavelength-interleaved optical continuum pulse set.

9. An optical pulse source according to claim 8 wherein the wavelength-tunable optical bandpass filter is configured to filter a plurality of the optical supercontinuum pulse sets in series to thereby form a repeating wavelength-interleaved optical supercontinuum pulse set.

10. An optical pulse source according to claim 1, wherein the optical pulse source further comprises a second gating device provided after the nonlinear optical element and configured to receive and pulse-pick optical supercontinuum pulses.

11. An optical pulse source according to claim 10, wherein the second gating device comprises an acousto-optical modulator, a wavelength-tunable optical bandpass filter, or an acousto-optic tunable filter.

12. An optical pulse source according to claim 10, wherein the second gating device is operable to reduce the optical intensity of one or more optical supercontinuum pulses in an optical supercontinuum pulse set.

13. A method of allowing a user to select the repetition rate of generating optical supercontinuum pulses generated by a source of optical supercontinuum pulses, comprising:
    generating a number of optical pump pulses having an associated repetition rate and a duration with a pump pulse source;
    gating the optical pump pulses to reduce the repetition rate; and
    introducing the gated optical pump pulses into a nonlinear optical element and generating therefrom optical supercontinuum pulses at the reduced repetition rate wherein the user can select the reduced repetition rate; and
    wherein the optical supercontinuum pulses have a supercontinuum spanning from below 450 nm to greater than 2000 nm.

14. The method of claim 13, where the optical supercontinuum pulses have an associated energy, the method further comprising:
scaling the optical supercontinuum pulse energy by increasing the pump pulse duration.

15. The method of claim 14, wherein scaling the energy of optical supercontinuum pulses further comprises reducing the repetition rate to less than 20 MHz and increasing the optical pump pulse duration to greater than 10 picoseconds.

16. The method of claim 15, wherein the pump pulse duration is increased to be at least 200 picoseconds.

17. An optical pulse source according to claim 1, wherein the optical pulse source is configured to generate output optical supercontinuum pulses at a repetition rate in the range 1 MHz to 10 MHz with an energy spectral density of at least 100 picojoules per nanometer, and the optical pulse source is configured to provide an illumination source for a stimulated emission depletion (STED) microscope.

18. An optical pulse source according to claim 17, wherein the optical pulse source further comprises a controller configured to scale the energy of the optical supercontinuum pulses by reducing the pump pulse repetition rate of the optical pump laser and increasing the pump pulse duration.

19. An optical pulse source according to claim 17, wherein the optical pump pulse repetition rate is less than 20 MHz, and the optical pump pulses have a duration of at least 200 picoseconds.

20. An optical pulse source according to claim 17, wherein the STED microscope is fluorescence-based, and wherein the illumination source provides excitation illumination and stimulated emission illumination.

21. An optical pulse source according to claim 1, wherein said optical pump laser generates said number of optical pump pulses at a pump pulse repetition rate R and wherein said user selectable repetition rate is R/N, where N is a positive integer.

22. An optical pulse source according to claim 1, wherein the optical pulse source comprises an all fiber configuration.

23. An optical pulse source according to claim 1, wherein said optical pump laser comprises an optical fiber oscillator and wherein the optical pulse source comprises an optical fiber amplifier between the optical fiber oscillator and said non-linear optical element and wherein said gating device is provided between the optical fiber oscillator and said optical fiber amplifier.

24. An optical pulse source according to claim 1, including a plurality of optical fiber amplifiers, and wherein said gating device is located before one of the plurality of optical fiber amplifiers located before said non-linear optical element and after another of the plurality of optical fiber amplifiers located before said non-linear optical element.

25. The method of claim 13, comprising making use of the optical supercontinuum pulses to perform fluorescent lifetime imaging (FLIM), time correlated fluorescence single photon counting (TCSPC), or stimulated emission depletion (STED) microscopy.

26. The method of claim 25, wherein making use of the optical supercontinuum pulses comprises performing FLIM.

27. The method of claim 25, wherein making use of the optical supercontinuum pulses comprises performing STED microscopy.

28. The method of claim 25, wherein making use of the optical supercontinuum pulses comprises performing TCSPC.

29. The method of claim 25, comprising amplifying the gated optical pump pulses before introducing the gated optical pump pulses to the nonlinear optical element.

30. The method of claim 29, comprising amplifying the optical pump pulses before the step of gating the optical pump pulses to reduce the repetition rate.

31. The method of claim 29, wherein amplifying the gated optical pump pulses comprises amplifying the gated optical pump pulses with an optical fiber amplifier wherein the peak power of a pulse that can be amplified is clamped, and wherein the duration of the gated optical pulses is selected such that the peak power of the gated optical pulses is within the peak power clamp.

32. The method of claim 31, wherein the duration of the gated optical pulses is hundreds of picoseconds.

33. The method of claim 32, wherein making use of the supercontinuum pulses comprises performing STED microscopy.

34. An optical pulse source according to claim 23 comprising a wavelength-tunable optical bandpass filter configured to receive at least one optical supercontinuum pulse and to wavelength filter the at least one optical supercontinuum pulse at a predetermined wavelength.

35. An optical pulse source according to claim 23 comprising a second gating device provided after the nonlinear optical element.

36. An optical pulse source according to claim 35 comprising a wavelength-tunable optical bandpass filter configured to receive at least one optical supercontinuum pulse and to wavelength filter the at least one optical supercontinuum pulse at a predetermined wavelength.

37. An optical pulse source according to claim 24 comprising a wavelength-tunable optical bandpass filter configured to receive at least one optical supercontinuum pulse and to wavelength filter the at least one optical supercontinuum pulse at a predetermined wavelength.

38. An optical pulse source according to claim 24 comprising a second gating device provided after the nonlinear optical element.

39. An optical pulse source according to claim 38 comprising a wavelength-tunable optical bandpass filter configured to receive at least one optical supercontinuum pulse and to wavelength filter the at least one optical supercontinuum pulse at a predetermined wavelength.

40. The method of claim 13 wherein
the associated repetition rate comprises the repetition rate R;
wherein gating the optical pump pulses to reduce the repetition rate comprises reducing the repetition rate to R/N, where N is a positive integer; and
wherein introducing the gated optical pump pulses into the nonlinear optical element and generating therefrom optical supercontinuum pulses at the reduced repetition rate comprises generating the optical supercontinuum pulses at the reduced rate R/N.

41. An optical pulse source for generating optical supercontinuum pulses at a repetition rate, comprising:
an optical pump laser operable to generate a number of optical pump pulses at a pump pulse repetition rate;
a nonlinear optical element arranged to receive the optical pump pulses and configured to generate therefrom optical supercontinuum pulses;
a gating device provided between the pump laser and the nonlinear optical element and operable to selectively limit the number of optical pump pulses received by the nonlinear optical element in order to generate optical supercontinuum pulses at a user selectable repetition rate lower than the pump pulse repetition rate;
a first optical fiber amplifier located before the nonlinear optical element;

a second optical fiber amplifier located before the nonlinear optical element; and wherein the gating device is located between the first and second optical fiber amplifiers.

42. A method of allowing a user to select the repetition rate of generating optical supercontinuum pulses generated by a source of optical supercontinuum pulses, comprising:

generating a number of optical pump pulses having an associated repetition rate and a duration with a pump pulse source;

gating the optical pump pulses to reduce the repetition rate;

introducing the gated reduced repetition rate optical pump pulses into a nonlinear optical element and generating therefrom optical supercontinuum pulses at the reduced repetition rate wherein the user can select the reduced repetition rate, wherein the method further comprises amplifying the optical pump pulses before the step of gating the optical pump pulses to reduce the repetition rate; and amplifying the gated optical pump pulses before introducing the gated optical pump pulses to the nonlinear optical element.

43. The optical pulse source according to claim 41 wherein the optical pulse source further comprises a wavelength-tunable optical bandpass filter configured to receive at least one optical supercontinuum pulse and to wavelength filter the at least one optical supercontinuum pulse at a predetermined wavelength.

44. The optical pulse source according to claim 41 wherein said non-linear optical element comprises an optical fiber and wherein said optical pulse source is configured such that optical pump pulses are launched into said optical fiber without the use of free space optics.

45. The method of claim 42 further comprising making use of the optical supercontinuum pulses to perform fluorescent lifetime imaging (FLIM), time correlated fluorescence single photon counting (TCSPC), or stimulated emission depletion (STED) microscopy.

46. The method of claim 45, wherein making use of the optical supercontinuum pulses comprises performing FLIM.

47. The method of claim 45, wherein making use of the optical supercontinuum pulses comprises performing STED microscopy.

48. The method of claim 45, wherein making use of the optical supercontinuum pulses comprises performing TCSPC.

* * * * *